US010874412B2

(12) United States Patent
Beck

(10) Patent No.: US 10,874,412 B2
(45) Date of Patent: Dec. 29, 2020

(54) SURGICAL INSTRUMENT AND REMOVABLE END EFFECTOR APPARATUS

(71) Applicant: Titan Medical Inc., Toronto (CA)

(72) Inventor: Kent F. Beck, Layton, UT (US)

(73) Assignee: TITAN MEDICAL INC., Toronto (CA)

( * ) Notice: Subject to any disclaimer, the term of this patent is extended or adjusted under 35 U.S.C. 154(b) by 190 days.

(21) Appl. No.: 16/110,883

(22) Filed: Aug. 23, 2018

(65) Prior Publication Data

US 2020/0060706 A1 Feb. 27, 2020

(51) Int. Cl.
*A61B 17/29* (2006.01)
*A61B 34/30* (2016.01)
*A61B 17/00* (2006.01)
*A61B 18/00* (2006.01)

(52) U.S. Cl.
CPC ............. *A61B 17/29* (2013.01); *A61B 34/30* (2016.02); *A61B 2017/00314* (2013.01); *A61B 2017/00473* (2013.01); *A61B 2017/00477* (2013.01); *A61B 2017/292* (2013.01); *A61B 2017/2927* (2013.01); *A61B 2017/2946* (2013.01); *A61B 2017/2948* (2013.01); *A61B 2018/00172* (2013.01); *A61B 2034/305* (2016.02)

(58) Field of Classification Search
CPC ... A61B 17/29; A61B 17/00234; A61B 34/30; A61B 2018/00172; A61B 2017/2948; A61B 2017/292; A61B 2017/2927; A61B 2017/00473; A61B 2017/00477; A61B 2017/2946; A61B 2017/00314; A61B 2017/2931; A61B 2017/2922; A61B 2034/305; A61B 17/282; A61B 17/2909; A61B 2017/0046

See application file for complete search history.

(56) References Cited

U.S. PATENT DOCUMENTS

| | | | |
|---|---|---|---|
| 5,318,570 A * | 6/1994 | Hood ................. | A61B 17/8847 606/99 |
| 5,522,788 A | 6/1996 | Kuzman | |
| 5,893,874 A * | 4/1999 | Bourque .............. | A61B 17/29 606/170 |
| 7,494,461 B2 * | 2/2009 | Wells .................. | A61B 17/122 600/104 |
| 8,025,621 B2 | 9/2011 | Ewaschuk et al. | |
| 8,257,386 B2 * | 9/2012 | Lee .................... | A61B 17/2909 606/205 |

(Continued)

FOREIGN PATENT DOCUMENTS

| WO | WO 99/15089 | 4/1999 |
|---|---|---|
| WO | WO 2014/201538 | 12/2014 |

(Continued)

*Primary Examiner* — Katherine H Schwiker
*Assistant Examiner* — Alexis D Amechi

(57) ABSTRACT

A surgical instrument apparatus includes an elongate tubular body having a proximal end and a distal end and a bore extending through the tubular body; an actuator link extending through and configured to move longitudinally within the bore, the actuator link including a first end connected to a first actuator at the proximal end of the tubular body and a second end terminating in a coupler, wherein the first end of the first actuator causes the actuator link to selectively move between an extended state and a retracted state.

10 Claims, 5 Drawing Sheets

(56) References Cited

U.S. PATENT DOCUMENTS

| | | | |
|---|---|---|---|
| 8,573,465 B2 | 11/2013 | Shelton | |
| 10,617,483 B2* | 4/2020 | Kadokura | A61B 34/30 |
| 2003/0097146 A1* | 5/2003 | Montalvo | A61B 10/06 |
| | | | 606/205 |
| 2015/0088191 A1* | 3/2015 | Coe | A61B 17/00234 |
| | | | 606/205 |
| 2016/0143633 A1* | 5/2016 | Robert | A61M 25/0147 |
| | | | 604/95.04 |

FOREIGN PATENT DOCUMENTS

| | | |
|---|---|---|
| WO | WO 2016/090456 | 6/2016 |
| WO | WO 2017/156618 A1 | 9/2017 |

* cited by examiner

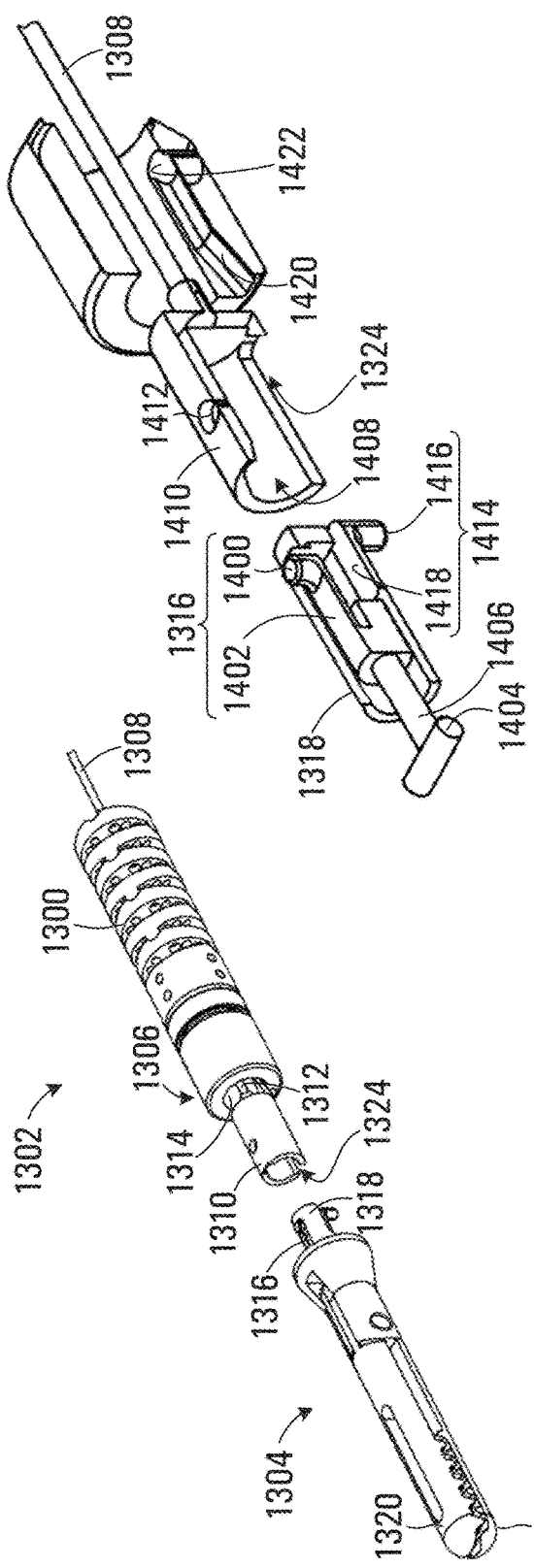
FIG. 13
FIG. 14
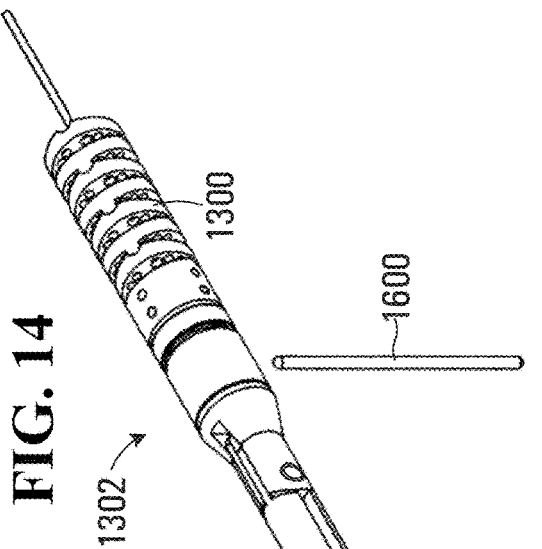
FIG. 15
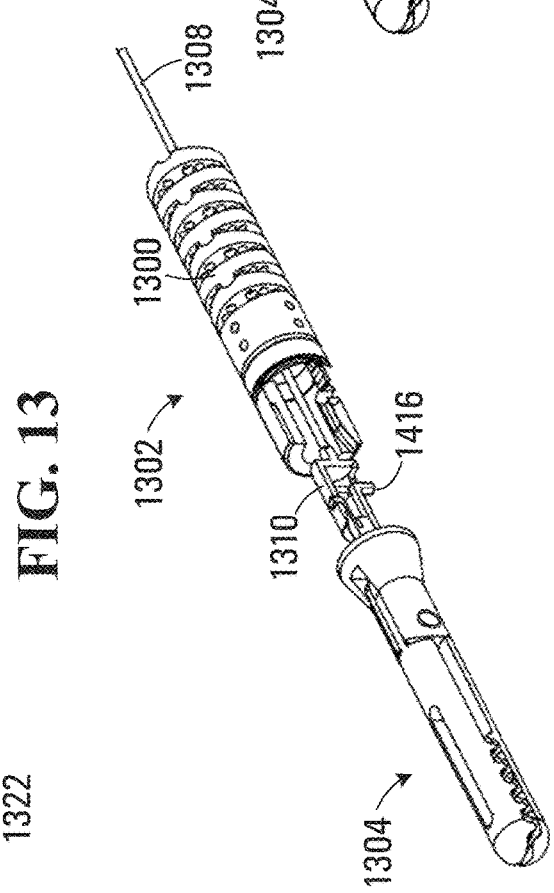
FIG. 16

SURGICAL INSTRUMENT AND REMOVABLE END EFFECTOR APPARATUS

BACKGROUND

1. Field

This disclosure relates generally to end effectors for surgical instruments and more specifically to a removable end effector for a surgical instrument.

2. Description of Related Art

Remotely actuated surgical instruments may be used in laparoscopic and/or robotic surgery. Robotic surgical systems commonly employ one or more instruments assemblies that are manipulated by a robotic system to perform surgical procedures. Each instrument is generally equipped with an end effector, such as a surgical scissor, forceps, dissector, or other end effector for performing surgical operations during the procedure. The end effector and a portion of the surgical instrument are typically inserted through an incision into a body cavity of a patient while an actuator portion of the instrument generally remains outside the body cavity. In many cases the instrument may be configured to accept any of a plurality of different end effectors, but changing the end effector attached may require some disassembly of the instrument.

SUMMARY

In accordance with some embodiments, there is provided a surgical instrument apparatus. The apparatus includes an elongate tubular body having a proximal end and a distal end and a bore extending through the tubular body. The apparatus also includes an actuator link extending through the bore and operably configured to move longitudinally within the bore, the actuator link having a first end connected to an actuator at the proximal end of the tubular body and a second end terminating in a coupler. The actuator is operably configured to cause the actuator link to selectively move between an extended state in which the coupler extends beyond the distal end of the tubular body to permit an end effector to be coupled to the coupler, and a retracted state in which the coupler is retracted back into the distal end of the tubular body for operation of the surgical instrument.

In the retracted state the actuator may be operably configured to cause pushing and pulling movements of the actuator link and the coupler, when coupled to the end effector, may be operable to cause movement of at least one moveable jaw of the end effector for performing surgical operations.

The actuator may include a first actuator operably configured to selectively cause the actuator link to move between the extended state and the retracted state and a second actuator operably configured to cause the pushing and pulling movement of the actuator link in the retracted state.

The first end of the actuator link may be connected to a slide mounted for longitudinal movement and the first actuator may include a leadscrew operable to rotate to cause longitudinal movement of the slide for causing the actuator link to move between the extended state and the retracted state.

The apparatus may include a lever extending transversely with respect to the leadscrew for causing rotation of the leadscrew.

The second actuator may include a linear actuator disposed for transverse movement with respect to the longitudinal movement of the slide, the linear actuator being coupled to the slide such that the transverse movement of the linear actuator causes longitudinal movement of the slide.

The second actuator may be coupled via a pin slidingly received within an angled channel in the slide.

At least a portion of the tubular body may include a manipulator responsive to movement of a plurality of control links extending along a length of the tubular body to cause movement of a distal end of the tubular body.

The coupler may include a ball mounted at the second end of the actuator link, the ball having a diameter larger than a diameter of the actuator link and operably configured to be received within a socket disposed on an actuation rod of an end effector such that when the actuator link is retracted the ball causes a corresponding retraction of the end effector and subsequent pushing and pulling movement of the actuator link causes movement of the actuation rod of the end effector.

The tubular body may include a threaded portion at the distal end and the ball, when received within the socket, facilitates rotation of the end effector to cause a corresponding threaded portion of the end effector to engage the threaded portion at the distal end of the tubular body for coupling the end effector to the apparatus.

Each of the tubular body and the end effector may include respective wrench flats operable to receive a wrench for applying a tightening torque to the end effector.

The tubular body may include a tapered bore for receiving a corresponding conical taper portion of the end effector, the tapered bore and conical taper being configured to provide a frictional retaining force for retaining the end effector in the tubular body when engaged.

At least one of the tubular body and the end effector may be operably configured to provide opposing surfaces that can be levered apart using a tool to separate the conical taper and tapered bore when removing the end effector from the tubular body.

The coupler may be operably configured to connect to an end effector via a snap-fit connection including a first resilient element disposed on one of the coupler and the end effector.

The first resilient element may include a cantilevered resilient element.

The first resilient element may include a surface operably configured to cause the end effector to be released when engaged by a tool.

The coupler may be operably configured to connect to the tubular body via a snap-fit connection including a second resilient element disposed on one of the coupler, the end effector, and the tubular body.

The second resilient element may include a cantilevered resilient element.

The second resilient element may include a surface operably configured to cause the coupler to be released when engaged by a tool.

The coupler may include a magnet mounted at the second end of the actuator link, the magnet being operable to couple to a corresponding magnet on the end effector.

The actuator link may include one of a stranded cable, a single strand cable, and a cable including a single strand portion and a stranded portion.

In accordance with some embodiments, there is provided a removable end effector apparatus for a surgical instrument. The apparatus includes an end effector body, and at least one moveable jaw mounted within the end effector body, the moveable jaw being operably configured to receive and connect to a coupler on a distal end of an actuator link of the surgical instrument when extended beyond a distal end of a tubular body of the surgical instrument. When the actuator link is retracted back into the distal end of the tubular body, the at least one moveable jaw is operably configured to move in response to pushing and pulling movements of the actuator link.

The coupler may include a ball disposed on the distal end of the actuator link and the end effector may include a socket for receiving the ball, the socket being mechanically coupled via an actuation rod to the at least one moveable jaw to cause movement of the least one moveable jaw.

The end effector may include a threaded portion and the socket may facilitate rotation of the end effector about the ball to cause the threaded portion of the end effector to engage a corresponding threaded portion at the distal end of the tubular body for connecting the end effector to the surgical instrument.

Each of the end effector and the tubular body may include respective wrench flats operable to receive a wrench for applying a tightening torque to the end effector.

The end effector may include a conical taper portion operably configured to engage a tapered bore in the distal end of the tubular body.

At least one of the end effector and the tubular body may be operably configured to provide opposing surfaces that can be levered apart using a tool to separate the conical taper and tapered bore when removing the end effector from the tubular body.

The end effector may be operably configured to connect to the coupler via a snap-fit connection including a first resilient element disposed on one of the coupler and the end effector.

The first resilient element may include a cantilevered resilient element.

The first resilient element may include a surface operably configured to cause the end effector to be released when engaged by a tool.

The coupler may be operably configured to connect to the tubular body via a snap-fit connection including a second resilient element, the second resilient element being disposed on the end effector.

The second resilient element may include a cantilevered resilient element.

The second resilient element may include a surface operably configured to cause the coupler to be released from the tubular body when engaged by a tool.

The end effector may include a magnet operable to couple to a magnet mounted at the distal end of the actuator link.

In accordance with some embodiments, there is provided a method of connecting an end effector to a surgical instrument, the surgical instrument including an elongate tubular body having a proximal end and a distal end and a bore extending through the tubular body. The method involves causing an actuator to move an actuator link longitudinally within the bore to cause a coupler disposed at a distal end of the actuator link to move to an extended state where the coupler extends beyond a distal end of the tubular body to permit an end effector to be connected to the coupler, and causing the actuator to move the actuator link longitudinally within the bore to cause the coupler to move to a retracted state in which the coupler is retracted back into the distal end of the tubular body for operation of the surgical instrument.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments,

FIG. 13 is an enlarged perspective view of a tubular body of a surgical instrument in accordance with another disclosed embodiment along with a disconnected end effector;

FIG. 14 is an partly cut away perspective view of coupling elements of the surgical instrument and end effector shown in FIG. 13;

FIG. 15 is an enlarged perspective view of the tubular body of the surgical instrument shown in FIG. 13 along with a partly connected end effector; and FIG. 16 is an enlarged perspective view of the tubular body of the surgical instrument shown in FIG. 13 along with a fully connected end effector.

DETAILED DESCRIPTION

Figure 1:
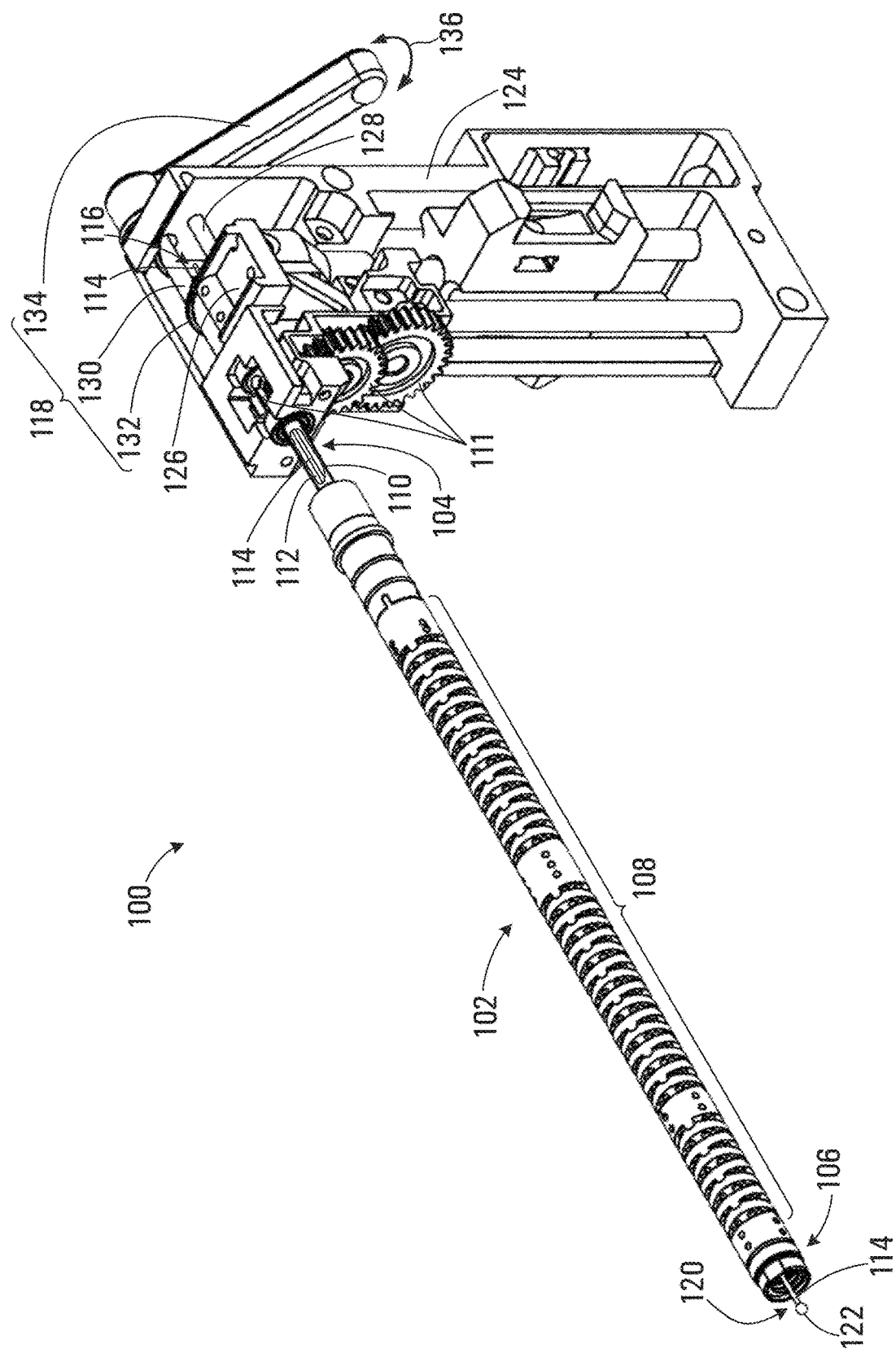
FIG. 1 is a perspective view of a surgical instrument in an extended state in accordance with one disclosed embodiment.
Figure 2:
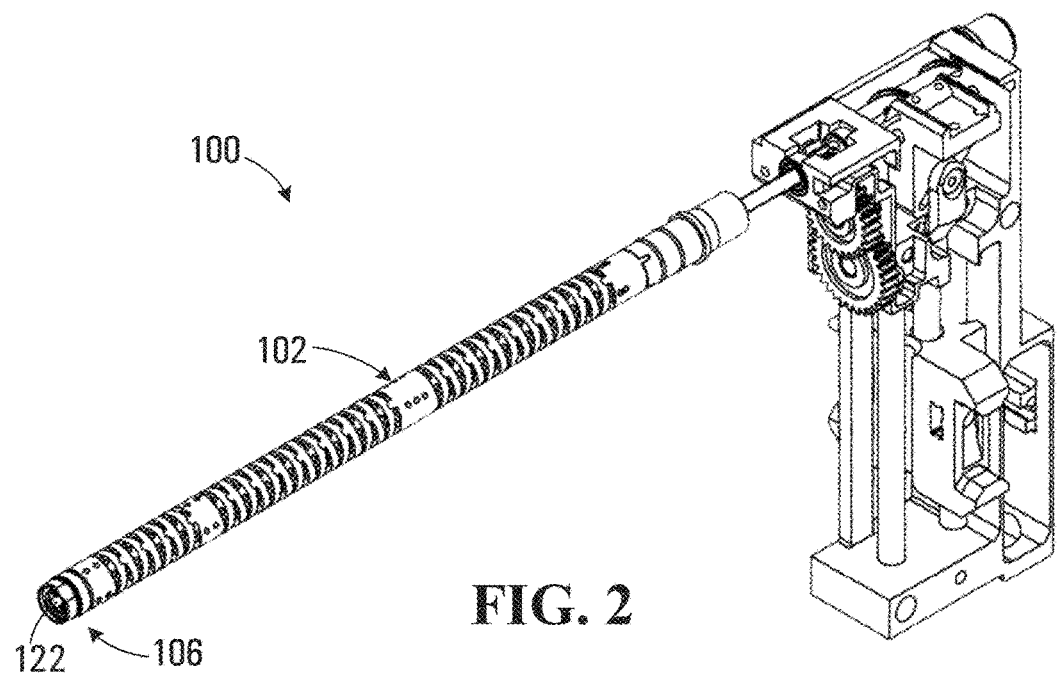
FIG. 2 is a perspective view of the surgical instrument shown in FIG. 1 in a retracted state.

Referring to FIG. 1 and FIG. 2, a surgical instrument apparatus according to a first disclosed embodiment is shown generally at 100. The surgical instrument 100 includes an elongate tubular body 102 having a proximal end 104 and a distal end 106. The surgical instrument 100 will typically have an end effector attached (not shown in FIG. 1) and will be inserted through an incision in a wall of the body cavity of a patient for performing surgical tasks within the body cavity.

In this embodiment the tubular body 102 of the surgical instrument 100 includes a manipulator 108 and a torque tube 110 extending through a central portion of the manipulator. The manipulator 108 may be responsive to movement of a plurality of control links (not shown) extending along a length of the tubular body to cause movement of a distal end of the tubular body as described in commonly owned PCT patent application PCT/CA2013/001076, entitled "Articulated Tool Positioner and System Employing Same", filed on 20 Dec. 2013. In such embodiments the torque tube 110 would be fabricated at least in part from a flexible material or structure that allows the torque tube to flex within the manipulator 108. In this embodiment the torque tube 110 is coupled to a gear train 111 for actuating rotation of the torque tube. In other embodiments the tubular body 102 may be otherwise configured or may not include the manipulator 108. For example the tubular body 102 may be rigid and the surgical instrument 100 may be partially inserted and moved as a unit for movement of the end effector within the body cavity of the patient.

The torque tube 110 has a bore 112 (shown in cut away view in FIG. 1) extending longitudinally through the torque tube 110 and tubular body 102. An actuator link 114 extends through the bore 112 and is able to move longitudinally within the bore. A first end 116 of the actuator link 114 is coupled to an actuator 118 disposed at the proximal end 104 of the tubular body and a second end 120 terminates in a coupler 122. The actuator 118 is operably configured to cause the actuator link 114 to selectively move between an extended state and a retracted state. The actuator link 114 may be implemented using a stranded cable, a single strand cable or rod, or a cable having both a single strand portion and a stranded portion.

The surgical instrument 100 is shown with the actuator link 114 in the extended state in FIG. 1, where the coupler 122 extends beyond the distal end 106 of the tubular body 102. The extended state permits connection of an end effector to the surgical instrument 100, as described in more detail below.

The surgical instrument 100 is shown in FIG. 2 with the actuator link 114 in the retracted state. Referring to FIG. 2, the actuator link 114 and coupler 122 has been retracted back into the distal end 106 of the tubular body 102. For surgical operations, an end effector will typically be attached to the surgical instrument 100. In FIG. 2 the end effector has been omitted to show the coupler 122 and actuator link 114 in the retracted state.

Referring back to FIG. 1, the actuator 118 is mounted on an actuator frame 124, which in the embodiment shown also carries a plurality of other actuator elements described in more detail later herein. In this embodiment the actuator link 114 is connected to a slide 126 received on a rod 128 mounted within the frame 124. The slide 126 is configured for longitudinal movement back and forth along the rod 128 and causes corresponding longitudinal movement of the actuator link 114 within the bore 112. The actuator 118 includes a leadscrew 130 having a coarse thread 132, that when rotated causes longitudinal movement of the slide 126 that causes the actuator link 114 to move between the extended state and the retracted state. The surgical instrument 100 also includes a lever 134 connected to and extending transversely with respect to the leadscrew 130 for causing rotation of the leadscrew when rotated in as indicated by the arrow 136.

Figure 3:
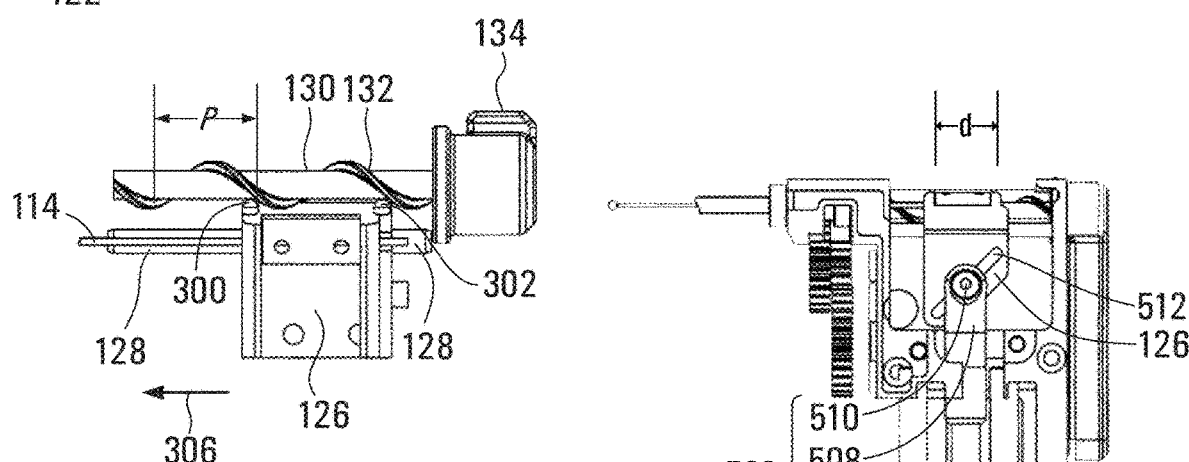
FIG. 3 is a plan view of an actuator and slide of the surgical instrument in the retracted state shown in FIG. 2.

Referring to FIG. 3, the actuator 118 and slide 126 are shown in plan view with the frame 124 omitted for sake of illustration. The slide 126 includes protrusions 300 and 302 that are sized and disposed to be engaged by the thread 132 on the leadscrew 130. When the lever 134 is rotated in the direction shown by the arrow 304 (FIG. 4), rotation of the leadscrew 130 causes the thread 132 to bear on the protrusions 300 and 302 moving the slide 126 along the rod 128 in the direction of the arrow 306 and causing the actuator link 114 to be extended longitudinally along the bore 112.

Figure 4:
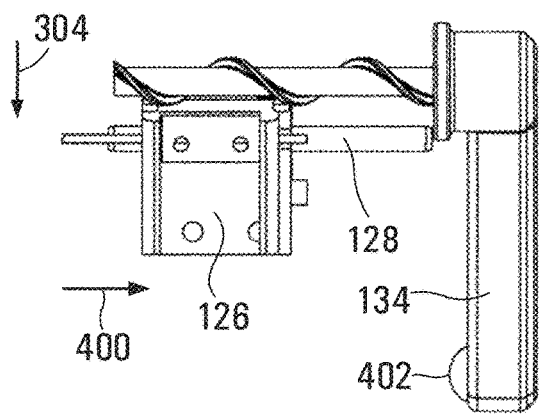
FIG. 4 is a plan view of the actuator and slide of the surgical instrument in the extended state shown in FIG. 1.

When the slide 126 reaches the extent of its longitudinal range of travel as shown in FIG. 4, the actuator link 114 will be in the extended state. Rotation of the lever 134 back in a direction opposite to the direction 304 causes the slide 126 to move in a direction indicated by the arrow 400, thus returning to the state shown in FIG. 3 where the actuator link 114 will be in the retracted state. The fairly coarse thread 132 on the leadscrew 130 requires a relatively small rotational movement of the lever 134 to move the slide 126 over the range of its travel causing the actuator link 114 to move between the retracted and extended states.

Figure 5:
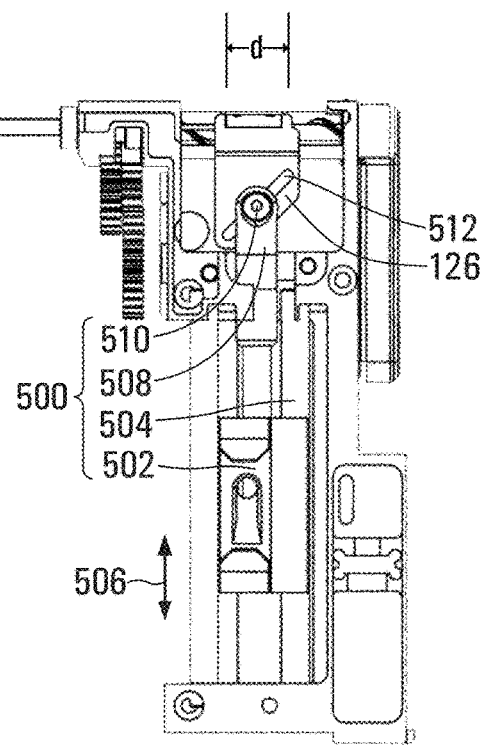
FIG. 5 is an elevational view of a frame of an actuator portion of the surgical instrument shown in FIG. 1 and FIG. 2.

The actuator frame 124 is shown in elevational view in FIG. 5 with the slide 126 disposed to place the actuator link 114 in the retracted state. Referring to FIG. 5, in the embodiment shown the actuator 118 (i.e. the leadscrew 130, thread 132 and lever 134) acts as a first actuator operably configured to selectively cause the actuator link 114 to move between the extended state and the retracted state. In this embodiment, the surgical instrument 100 also includes a second actuator 500, which is implemented as a linear actuator 500 that moves in a transverse direction with respect to the longitudinal movement of the slide 126. The second actuator 500 includes a traversing element 502 mounted on a rod 504 for movement in a transverse direction indicated by the arrow 506. The traversing element 502 is coupled to a yoke 508 having a pin 510 received within an angled channel 512 in the slide 126. Transverse movement of the traversing element 502 in the direction 506 is thus coupled via the yoke 508 and pin 510 to cause longitudinal movement of the slide 126. Upward movement of the traversing element 502 on the rod 504 thus causes the slide 126 to move toward the distal end 106 of the tubular body 102 (i.e. direction 306 in FIG. 3). Downward movement of the traversing element 502 causes the slide 126 to move rearwardly (i.e. direction 400 in FIG. 4).

When actuator link 114 is in the retracted state, the lever 134 may be constrained from further rotation by a detent. For example, the lever 134 may include a spherical protrusion 402 (FIG. 4) that is received within a spring detent mechanism (not shown) on the frame 124 that receives the protrusion and constrains the lever 134 from being inadvertently moved. Due to the relatively coarse thread pitch of the threads 132 on the leadscrew 130, the slide 126 will still be able to move over a range equal to the thread pitch (the thread pitch is indicated as "P" in FIG. 3) while the lever 134 is held by the detent and the actuator link 114 is in the retracted position. In the retracted state, the slide 126 and actuator link 114 are thus responsive to movement of the traversing element 502 for movement over a longitudinal range of motion d as indicated in FIG. 5. The range of motion d may be constrained by the length of the angled channel 512, which may be slightly less than the thread pitch P.

Generally, the linear actuator 500 facilitates a movement d that would be less than the extension and retraction movement caused by the first actuator 118 and this movement is used to actuate the end effector, as described in more detail later herein. The lever 134 will generally only be operated to during preparations for a surgical procedure i.e. to move the actuator link 114 into the extended state for attaching an end effector. Once the end effector 600 is attached, the actuator link 114 of the surgical instrument 100 will be returned to the retracted state and the lever 134 held in the retracted position. During the surgical procedure, transverse movement of the traversing element 502 may be caused by a drive force received at the traversing element 502 from an instrument driver (not shown) and further attempts to move the slide 126 through operation of the lever 134 would be constrained by the coupling of the traversing element 502 to the instrument drive.

Figure 6:
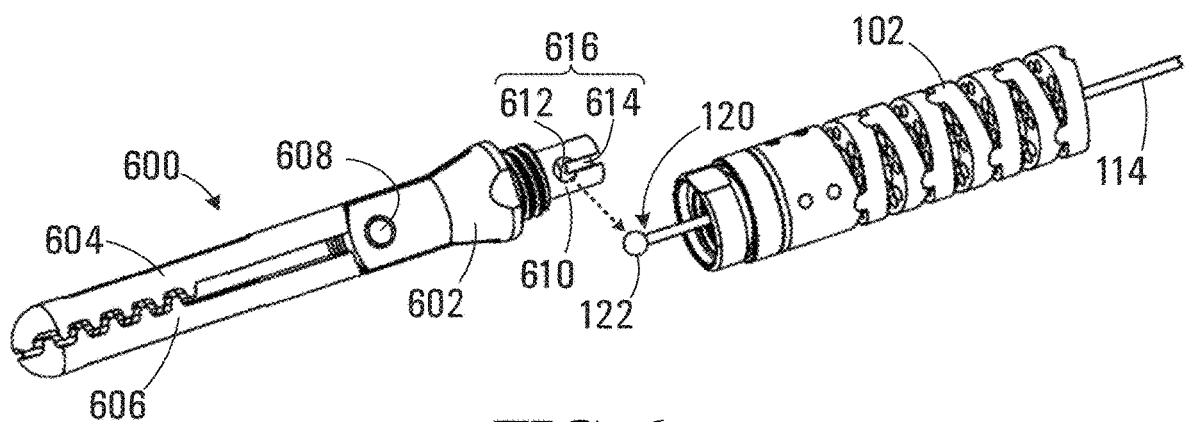
FIG. 6 is an enlarged perspective view of a tubular body of the surgical instrument shown in FIG. 1 along with a disconnected end effector.

An enlarged view of the distal end 106 of the tubular body 102 with the actuator link 114 in the extended state is shown in FIG. 6 along with an initially disconnected end effector 600. Referring to FIG. 6, the end effector 600 includes a housing 602 and a pair of jaws 604 and 606 mounted for opening and closing movement about a common pivot 608. In the embodiment shown, the coupler 122 is implemented as a ball mounted at the second end 120 of the actuator link 114, the ball having a diameter larger than a diameter of the actuator link. The ball may be a stainless steel ball that is welded or crimped to the actuator link 114 or may be formed as a unitary part of the actuator link. The end effector 600 also includes an actuation rod 610, which includes a socket 616 having a spherical recess portion 612 for receiving the ball and a channel portion 614 for receiving the actuator link 114. When the actuator link 114 is in the extended state as shown, the ball of the coupler 122 is easily accessible for coupling into the socket 616 of the actuation rod 610.

Figure 7:
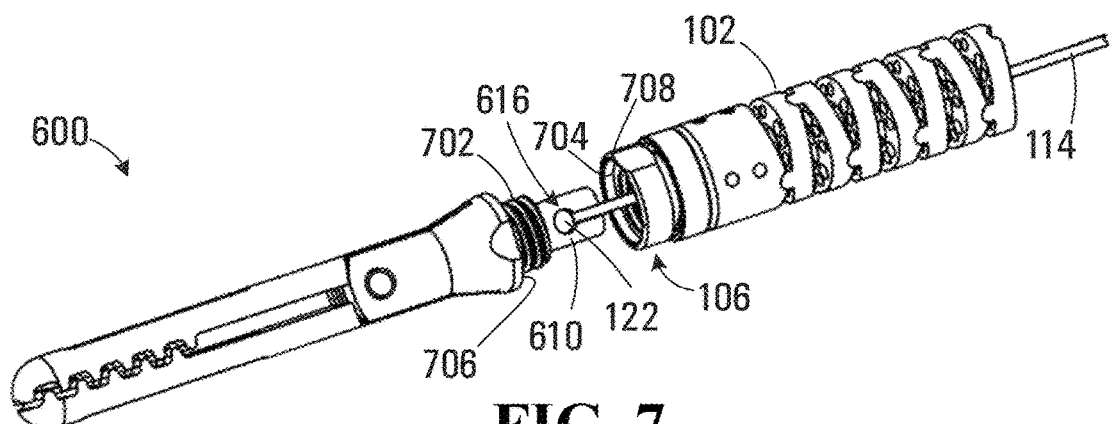
FIG. 7 is a further enlarged perspective view of the tubular body of the surgical instrument along with partly connected end effector.

Referring to FIG. 7, when the ball of the coupler 122 is received within the spherical recess 612 of the actuation rod 610, the lever 134 (FIG. 4) may be rotated to cause the actuator link 114 to be retracted in the direction indicated by arrow 700 (FIG. 8), thus causing the end effector 600 to move toward the distal end 106 of the tubular body 102. In this embodiment, the end effector 600 has a threaded portion 702 and the tubular body 102 has a corresponding threaded portion 704 at the distal end 106 of the tubular body 102.

Figure 8:
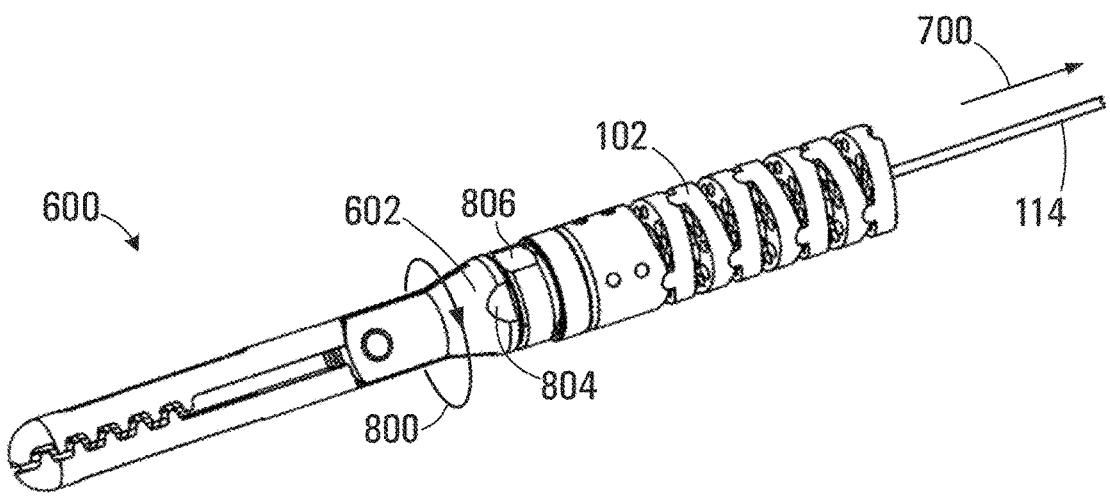
FIG. 8 is an enlarged perspective view of the tubular body of the surgical instrument along with a fully connected end effector.

Referring to FIG. 8, once the actuator link 114 has been retracted and the threaded portions 702 and 704 (FIG. 7) engaged, the end effector 600 is rotated as indicated by the arrow 800 to connect the end effector to the tubular body 102. The end effector 600 may be initially finger tightened to the tubular body 102. In this embodiment, the housing 602 of the end effector includes a pair of wrench flats (one of which is visible at 804) for receiving a first wrench (not shown). Similarly, the distal end 106 of the tubular body 102 also has a pair of wrench flats (one of which is visible at 806) for receiving a second wrench (also not shown). After the initial finger tightening, the first and second wrenches may be used to torque the end effector 600 to the tubular body 102 to prevent the end effector from becoming detached during a surgical procedure. The end surface 706 of the end effector 600 and the end surface 708 of the distal end 106 of the tubular body 102 thus effectively act as a jam nut. In one embodiment, one of the wrenches may be a torque wrench, configured to torque the end effector 600 to the tubular body 102 within a design torque specification.

In other embodiments, the socket 616 on the end effector 600 and ball of the coupler 122 may be exchanged such that the ball is made part of the end effector and the socket is disposed at the end of the actuator link 114.

As described above in connection with FIGS. 3-5, the second actuator 500 only becomes operational once the end effector 600 has been attached to the surgical instrument 100 and the surgical instrument attached to an instrument drive. When the surgical instrument 100 is configured to place the actuator link 114 in the retracted state, the second actuator 500 facilitates movement of the slide 126 though the distance d, as shown in FIG. 5. This movement of the slide 126 causes pushing and pulling movements of the actuator link 114 and the coupler 122, which is operable to actuate the end effector. The effect caused by the actuation depends on the configuration of the end effector. In the case of the end effector 600, actuation of the actuator link 114 causes a pair of jaws 604, 606 to move about the common pivot 608 for grasping tissue. In other embodiments the end effector may be a dissector having either a single moveable cutting blade or a pair of moveable cutting blades.

Figure 9:
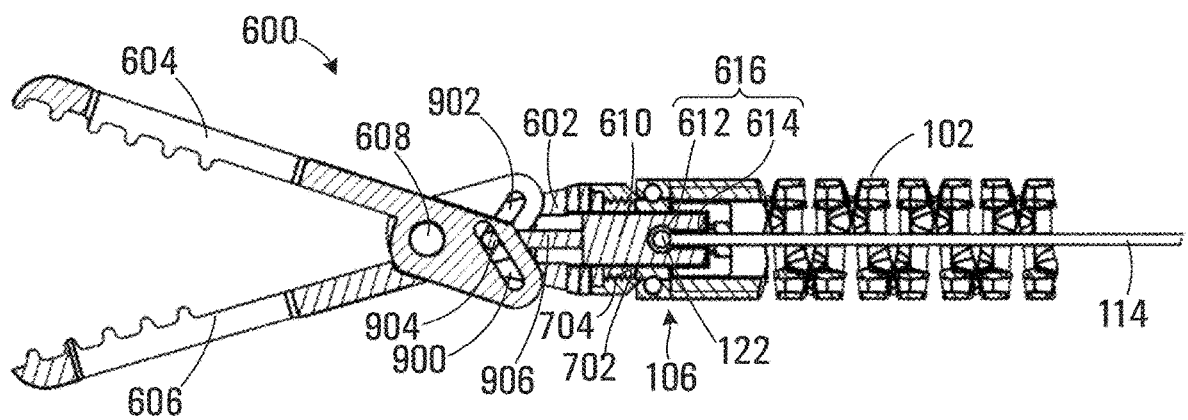
FIG. 9 is a cross sectional view of the fully connected end effector shown in FIG. 8.

Referring now to FIG. 9, the end effector 600 and a portion of the tubular body 102 of the surgical instrument 100 is shown in longitudinal cross section. The ball of the coupler 122 has been engaged within the socket 616 on the actuation rod 610. A portion of the actuation rod 610 on which the socket 616 is located is received within the distal end 106 of the tubular body 102 and a remaining portion is received within the housing 602 of the end effector 600 and configured for longitudinal sliding motion in response to movement of the actuator link 114. The threaded portions 702 and 704 have been engaged to secure the end effector 600 in the distal end 106 of the tubular body 102.

In the embodiment shown, each of the pair of jaws 604 and 606 has a respective slot 900 and 902 disposed rearwardly of the common pivot 608. A pin 904 extends laterally through the respective slots 900 and 902 and is connected to the actuation rod 610 via a link 906. Longitudinal movement of the actuator link 114 toward the distal end 106 of the tubular body 102 (i.e. a pushing movement) causes a corresponding movement of the actuation rod 610, which is coupled via the link 906 to the pin 904, causing the jaws to open. Similarly, longitudinal movement of the actuator link 114 away from the distal end 106 of the tubular body 102 (i.e. a pulling movement) causes the jaws to close.

Figure 10:
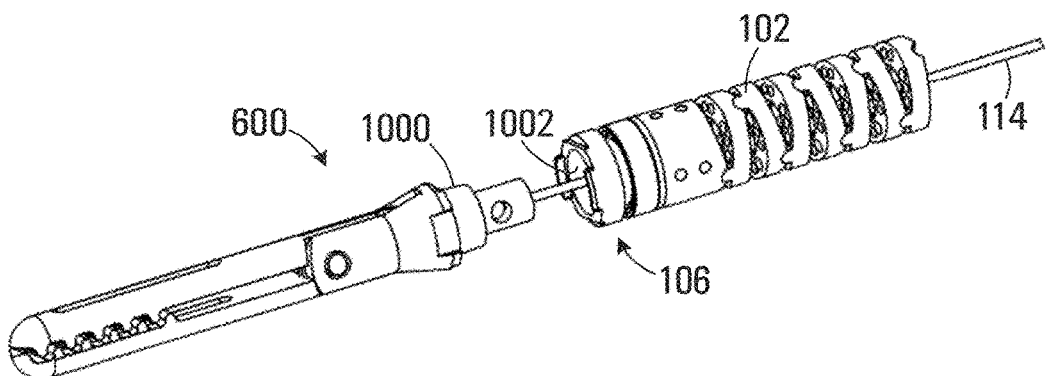
FIG. 10 is a perspective view of a tubular body and partly connected end effector in accordance with an alternative embodiment for coupling the end effector and tubular body.
Figure 11:
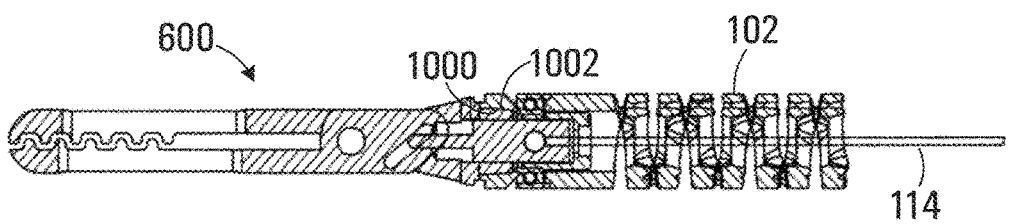
FIG. 11 is a cross sectional view of the end effector shown in FIG. 10 in a fully connected state.

Referring to FIG. 10, in an alternative embodiment the threaded portion 702 may be replaced with a tapered conical surface 1000 and the threaded portion 704 may be replaced with a corresponding tapered bore 1002. Tapered surfaces such as Luer tapers are used in medical equipment to implement sealed connections between components. The tapered conical surface 1000 and corresponding tapered bore 1002 may be sized such that when the end effector 600 is attached to the distal end 106 of the tubular body 102 the tapered conical surface 1000 is easily received within the tapered conical surface 1000 and corresponding tapered bore 1002. A cross sectional view of the connected end effector 600 and tubular body 102 via the tapered conical surface 1000 and tapered conical surface 1000 and corresponding tapered bore 1002 is shown in FIG. 11. Referring to FIG. 11, the tapered conical surface 1000 is fully engaged in the tapered bore 1002. The respective taper angles are controlled to ensure a close fit along the length of the taper that provides sufficient frictional retaining force to secure the end effector 600 in place.

Figure 12:
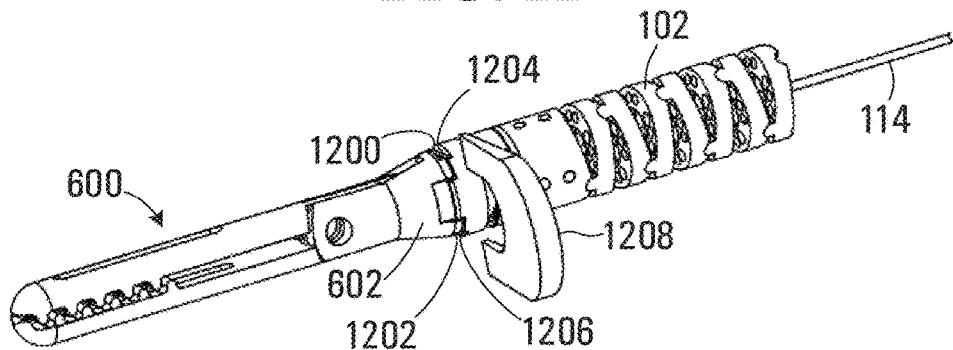
FIG. 12 is a perspective view of the fully connected end effector shown in FIG. 10.

Once the end effector 600 and tubular body 102 are attached, the tapered conical surface 1000 and corresponding tapered bore 1002 may be difficult to dislodge, particularly in cases where the taper angles are closely matched. Referring to FIG. 12, the housing 602 of the end effector 600 includes notches in the outer circumference of the housing 602 that provide surfaces 1200 and 1202 oriented toward the tubular body 102. A corresponding notch in the circumference of the distal end 106 of the tubular body 102 similarly provides surfaces 1204 and 1206. The surfaces 1204 and 1206 oppose the surfaces 1200 and 1202 and the notches are sized to permit a wedge tool 1208 to be received between the respective surfaces for disconnecting the end effector 600 from the tubular body 102. The wedge tool 1208 when received in the notches and moved laterally causes a longitudinal force to be applied between the surfaces 1200-1206 that is sufficient to overcome the frictional retaining forces between the tapered conical surface 1000 and tapered bore 1002.

An alternative coupling embodiment is shown in FIG. 13 in partly cut away view. In this embodiment the ball coupler 122 is replaced by a barrel-type coupler. Referring to FIG. 13, a tubular body 1300 of a surgical instrument 1302 is shown in part along with an end effector 1304. The end effector 1304 and tubular body 1300 are both generally configured as described above. In this embodiment however, the surgical instrument 1302 includes an actuator link 1308 having a barrel coupler 1310 attached to a distal end 1312 of the actuator link 1308. The barrel coupler 1310 is sized to be retractable within a bore 1314 on a distal end 1306 of the tubular body 1300. The surgical instrument 1302 is configured generally as described above and the actuator link 1308 and barrel coupler 1310 are also moveable between the extended state (as shown in FIG. 13) and the retracted state. In the embodiment shown, the end effector 1304 has a first resilient element 1316 disposed on an actuator rod 1318 of the end effector. The end effector 1304 includes a pair of moveable jaws 1320 and 1322 and the actuator rod 1318 actuates movement of the jaws of the end effector 1304, generally as described above in connection with FIG. 9. The actuator rod 1318 is configured to be received within the barrel coupler 1310 and is retained via a snap-fit connection provided by the first resilient element 1316.

The distal end 1306 of the tubular body 1300, barrel coupler 1310, and actuator rod 1318 are shown cut away in FIG. 14. Referring to FIG. 14, in this embodiment the first resilient element 1316 comprises a pin 1400 disposed at the end of a cantilevered beam 1402. The actuator rod 1318 also includes a pin 1404 connected to the actuator rod 1318 via a linkage 1406, which together operate to open and close the jaws 1320 and 1324 generally as described above in connection with FIG. 9. When connecting the end effector 1304 to the end effector 1304 and tubular body 1300, the actuator rod 1318 of the end effector 1304 is received in an opening 1408 of the barrel coupler 1310 and the pin 1400 bears against an upper surface 1410 of the coupler causing the cantilevered beam 1402 to deflect downwardly. The barrel coupler 1310 includes an opening 1412 sized to receive the pin 1400 for retaining the actuator rod 1318 within the barrel coupler 1310. The end effector 1304 is shown connected to the barrel coupler 1310 in FIG. 15, with the barrel coupler 1310 still in the extended state.

Referring back to FIG. 14, the actuator rod 1318 of the end effector 1304 also includes a second resilient element 1414, having a pin 1416 disposed at the end of a cantilevered beam 1418. The barrel coupler 1310 has a slot 1324 for receiving the pin 1416, which protrudes through the slot once the end effector 1304 is connected to the barrel coupler 1310, as shown in FIG. 15. The actuator link 1308 may then be retracted to cause the barrel coupler 1310 to be pulled back into the distal end 1306 of the tubular body 1300. The pin 1416 engages a channel 1420 in the distal end 1306 of the tubular body 102, which causes the cantilevered beam 1418 to deflect. The distal end 1306 of the tubular body 102 also has an opening 1422 sized to receive the pin 1416 for retaining the barrel coupler 1310 and connected end effector 1304 within the tubular body 102.

Referring to FIG. 16, the end effector 1304 is shown connected to the tubular body 1300 with the actuator link 1308 and barrel coupler 1310 in the retracted state ready for operation. Following use of the surgical instrument 1302 in a surgical procedure, the end effector may be removed using a pin tool 1600. The pin tool 1600 is sized to engage the pin 1416 within the opening 1422 in the distal end 1306 of the tubular body 1300 and thus release the end effector 1304 and barrel coupler 1310 from the tubular body. The surgical instrument 1302 may then be configured to place the actuator link 1308 in the extended state as described above thus providing access to the pin 1400. The pin 1400 may also be released using the pin tool 1600 releasing the end effector 1304 from the barrel coupler 1310.

In the embodiment shown in FIGS. 13-16, the first and second resilient elements 1316 and 1414 are both implemented on the end effector 1304. However in other embodiments the resilient elements may be disposed on either the barrel coupler 1310 or the distal end 1306 of the tubular body 1300.

In one embodiment, the end effectors 600 and 1304 may be designated as single use or limited use components that are received in a sterile packaging and connected to the respective surgical instruments 100, 1302. The used end effectors may be discarded once used. The surgical instruments 100, 1302 may however be designated for multiple uses and once the end effector is removed may be put through a sterilization process to ready the instruments for further use.

In another embodiment, the ball coupler 122 or barrel coupler 1310 may be omitted in favor of a coupler that employs magnets to make the connection between the end effector and surgical instrument. For example, annular ring magnets may be affixed to the actuation rod of the actuator and within the bore of the tubular body and may act to retain the end effector.

While specific embodiments have been described and illustrated, such embodiments should be considered illustrative only and not as limiting the disclosed embodiments as construed in accordance with the accompanying claims.

What is claimed is:

1. A surgical instrument apparatus comprising:
an elongate tubular body including a proximal end and a distal end and a bore extending through the tubular body;
an actuator link extending through the bore and configured to move longitudinally within the bore, the actuator link including a first end connected to an actuator at the proximal end of the tubular body and a second end terminating in a coupler, wherein the first end of the actuator link is connected to a slide mounted for longitudinal movement, wherein the actuator includes:
a first actuator; and
a second actuator;
wherein the first actuator is configured to cause the actuator link to selectively move between:
an extended state in which the coupler extends beyond the distal end of the tubular body to permit an end effector to be coupled to the coupler; and
a retracted state in which the coupler is retracted back into the distal end of the tubular body for operation of the surgical instrument; and
wherein:
the first actuator includes a leadscrew configured to rotate to cause longitudinal movement of the slide for causing the actuator link to move between the extended state and the retracted state,
when the actuator link is in the retracted state, the second actuator is configured to cause pushing and pulling movements of the actuator link, and wherein the coupler, when coupled to the end effector, is configured to cause movement of at least one moveable jaw of the end effector for performing surgical operations.

2. The apparatus of claim 1 further comprising a lever extending transversely with respect to the leadscrew for causing rotation of the leadscrew.

3. The apparatus of claim 1 wherein the second actuator comprises a linear actuator disposed for transverse movement with respect to the longitudinal movement of the slide, the linear actuator being coupled to the slide such that the transverse movement of the linear actuator causes longitudinal movement of the slide.

4. The apparatus of claim 3 wherein the second actuator is coupled to the slide via a pin slidingly received within an angled channel in the slide.

5. The apparatus of claim 1 wherein at least a portion of the tubular body comprises a manipulator responsive to movement of a plurality of control links extending along a length of the tubular body to cause movement of a distal end of the tubular body.

6. The apparatus of claim 1 wherein the coupler comprises a ball mounted at the second end of the actuator link, the ball having a diameter larger than a diameter of the actuator link and configured to be received within a socket disposed on an actuation rod of an end effector such that when the actuator link is retracted the ball causes a corresponding retraction of the end effector and subsequent pushing and pulling movement of the actuator link causes movement of the actuation rod of the end effector.

7. The apparatus of claim 6 wherein the tubular body comprises a threaded portion at the distal end and wherein the ball, when received within the socket, facilitates rotation of the end effector to cause a corresponding threaded portion of the end effector to engage the threaded portion at the distal end of the tubular body for coupling the end effector to the apparatus.

8. The apparatus of claim 7 wherein each of the tubular body and the end effector comprise respective wrench flats configured to receive a wrench for applying a tightening torque to the end effector.

9. The apparatus of claim 6 wherein the tubular body comprises a tapered bore for receiving a corresponding conical taper portion of the end effector, the tapered bore and conical taper being configured to provide a frictional retaining force for retaining the end effector in the tubular body when engaged.

10. The apparatus of claim 9 wherein at least one of the tubular body and the end effector is configured to provide opposing surfaces that can be levered apart using a tool to separate the conical taper and tapered bore when removing the end effector from the tubular body.

* * * * *